(12) United States Patent
Bang et al.

(10) Patent No.: US 8,079,277 B2
(45) Date of Patent: Dec. 20, 2011

(54) APPARATUS AND METHOD FOR REFINING SUBJECT ACTIVITY CLASSIFICATION FOR RECOGNITION OF DAILY ACTIVITIES, AND SYSTEM FOR RECOGNIZING DAILY ACTIVITIES USING THE SAME

(75) Inventors: Sun Lee Bang, Daejeon (KR); Min Ho Kim, Daejeon (KR); Soo Jun Park, Seoul (KR); Seon Hee Park, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 790 days.

(21) Appl. No.: 12/105,327

(22) Filed: Apr. 18, 2008

(65) Prior Publication Data

US 2009/0082699 A1 Mar. 26, 2009

(30) Foreign Application Priority Data

Sep. 21, 2007 (KR) ............... 10-2007-0096510

(51) Int. Cl.
| | |
|---|---|
| A61B 5/00 | (2006.01) |
| A61B 5/103 | (2006.01) |
| A61B 5/117 | (2006.01) |
| G01L 5/16 | (2006.01) |
| G01N 33/48 | (2006.01) |
| G01C 17/38 | (2006.01) |
| H03F 1/26 | (2006.01) |
| H04B 15/00 | (2006.01) |

(52) U.S. Cl. ........... 73/865.4; 600/595; 702/19; 702/93; 702/189; 702/191

(58) Field of Classification Search .......... 600/595; 73/865.4; 702/19, 93, 189–197

See application file for complete search history.

(56) References Cited

U.S. PATENT DOCUMENTS

| | | | |
|---|---|---|---|
| 2004/0087878 A1 * | 5/2004 | Krausman et al. | ............ 600/587 |
| 2005/0054381 A1 | 3/2005 | Lee et al. | |
| 2006/0149905 A1 | 7/2006 | Park et al. | |
| 2006/0282021 A1 | 12/2006 | DeVaul et al. | |

FOREIGN PATENT DOCUMENTS

| | | |
|---|---|---|
| KR | 1020010035037 A | 5/2001 |
| KR | 1020020043051 A | 6/2002 |
| KR | 1020050025220 A | 3/2005 |
| KR | 1020060068518 A | 6/2006 |

OTHER PUBLICATIONS

Gorny, Stephen et al. "A parametric and sleep hysteresis approach to assessing sleep and wake from a wrist activity meter with enhanced frequency range." Association of Professional Sleep Scientists 10th Annual Meeting. 1996. Abstract No. 309.*

* cited by examiner

*Primary Examiner* — Max Hindenburg
*Assistant Examiner* — John Pani
(74) *Attorney, Agent, or Firm* — Ladas & Parry LLP

(57) ABSTRACT

Apparatus and method for refining subject activity classification for the recognition of daily activities of a subject, and a system for recognizing daily activities using the same. The refining apparatus improves the correctness of subject activity classification using daily activities of a subject, activation time information of sensors mounted on objects associated with the daily activities of the subject, and the suitability of a continuous activity pattern in relation to the daily activities. This improves the correctness of subject activity classification that becomes basic information in daily activity analysis.

11 Claims, 5 Drawing Sheets

APPARATUS AND METHOD FOR REFINING SUBJECT ACTIVITY CLASSIFICATION FOR RECOGNITION OF DAILY ACTIVITIES, AND SYSTEM FOR RECOGNIZING DAILY ACTIVITIES USING THE SAME

CROSS-REFERENCE TO RELATED APPLICATIONS

This application claims the priority of Korean Patent Application No. 10-2007-0096510, filed on Sep. 21, 2007, in the Korean Intellectual Property Office, the disclosure of which is incorporated herein by reference.

BACKGROUND OF THE INVENTION

1. Field of the Invention

The present invention relates to apparatus and method for refining subject activity classification for the recognition of daily activities of a subject, and a system for recognizing daily activities using the same, and more particularly, to refining apparatus and method for improving the correctness of subject activity classification using daily activities of a subject, activation time information of sensors mounted on objects associated with the daily activities of the subject, and the suitability of a continuous activity pattern in relation to the daily activities, and a system for recognizing daily activities using the same.

This work related to the present invention was supported by IT R&D Program of MIC/IITA [2006-S007-02, Ubiquitous Health Monitoring Module and System Development].

2. Description of the Related Art

Recently, in response to the development of ubiquitous computing environment and medical technologies, people become more interested in health care. For healthy lives, demands for a U-health care program and a health care service are sharply rising.

Owing to the sharply rising demands for the U-health care program and the health care service, a health care service is expanding from medical facilities to individuals or homes. In order to maintain a healthy life pattern and recognize an emergent situation, studies on the recognition of daily activities at home are actively being carried out.

As a study for recognizing daily activities, Radio Frequency IDentification (RFID) tags are attached to objects, which are associated with daily activities, and an RFID reader is attached to a user (i.e., a subject). When the subject touches an object, a corresponding daily activity is deduced from a response of the object.

The merit of this method is that the use information of an object, associated with a daily activity, can be directly acquired. However, this method does not consider an activity of the subject (hereinafter also referred to as "subject activity"), but merely recognizes the response of the object, which was read by the RFID reader.

In order to correctly recognize a specific daily activity, it is required, basically, to acquire not only a response of an object but also an activity of a subject.

That is, both a movement necessary for the subject to perform a specific daily activity and the response applied to the object should be considered in order to correctly recognize a daily activity.

For example, when the subject sits at a chair of table to have a meal, the activity of the subject should be recognized as the term 'sit,' and at the same time, a response indicating that something is placed on the chair should be acquired.

Recently, in order to analyze subject activities, a study is being carried out using three axis acceleration sensors or the like, which are worn on the waist or shoulders of the subject. Subject activities are measured from the sensors, and are classified by applying a statistical process to measurement data, so that detailed activities of the subject can be recognized.

In this method, however, a highly sensitive device can cause a data error, which degrades the correctness of daily activity classification.

As discussed above, the problems of the conventional method of using the RFID tag and the RFID reader are that the subject activity is not correctly deduced since only the response of the object, to which the RFID tag is attached, is considered, and the subject should wear a large RFID reader in daily life.

Moreover, in the conventional method of recognizing daily activities using the multiple sensors in order to improve the correctness of daily activity classification, only advancement is that the same sensors are attached to different positions. Accordingly, correct subject activity classification is not enabled.

SUMMARY OF THE INVENTION

The present invention has been made to solve the foregoing problems with the prior art, and therefore the present invention provides a refining apparatus for improving the correctness of subject activity classification using daily activities of a subject, measured by sensors attached to body of subject, and an use information of objects, associated with the daily activities of the subject and measured by the sensors mounted of the objects, that is, an activation time information of the sensors mounted on the objects, and the suitability of a continuous activity pattern in relation to the daily activities, a system for recognizing daily activities using the same, and a refining method of subject activity classification for the recognition of daily activities.

According to an aspect of the invention, there is provided an apparatus for refining subject activity classification, the apparatus includes: an input buffer receiving and storing activity classification values of activity data of a subject, measured by a sensor attached to a body of the subject, and object response data of objects associated with the activity data of the subject and measured by at least one sensor mounted on the objects; a first refining module extracting a predetermined section of the activity classification values, stored in the input buffer, extracting a sudden significant activity data, which occurs in a time shorter than a minimum time necessary for carrying out an activity corresponding to an activity classification value in the predetermined section, and refining the extracted sudden significant activity data to be identical with an activity classification values preceding and following the sudden significant activity data; and a second refining module, if the sudden significant activity data is absent in the predetermined section, extracting an unsuitable pattern, which is not suitable for a continuous activity pattern of the activity classification values in the predetermined section and refining the unsuitable pattern to be identical with the continuous activity pattern by considering an activation time of the sensor mounted on the objects associated with the activity data of the subject.

Each of the object response data and the activity classification values may include occurrence time information of an activity and an object response.

The first refining module may organize triple data by receiving, from the input buffer, three continuous activity classification values, which are extracted from the predetermined section and are time sequential, compare a short time activity data with a preceding activity classification value just prior thereto if the short time activity data is present in the triple data, judge the short time activity data as a sudden significant data if the short time activity data is not identical with the preceding activity classification value just prior thereto, and refine the sudden significant data using preceding and following activity classification values, which are classified as identical activities.

The second refining module may judge whether or not the triple data are suitable for a continuous activity pattern if the sudden significant data is absent in the triple data, and if there is an unsuitable pattern, refine the unsuitable pattern using a reference activity set to the triple data and an activation time of at least one sensor mounted on an object associated with the reference activity.

The second refining module may refine the activity classification value following the reference activity, using the reference activity, if at least one sensor mounted on an object associated with the reference activity is kept activated until an occurrence of the following activity classification value.

The second refining module may refine the unsuitable pattern by matching a suitable continuous activity pattern with the triple data, if at least one sensor mounted on an object associated with the reference activity is not kept activated until an occurrence of the following activity classification value.

The second refining module may preferentially set an activity, in which an object response data is simultaneously activated during an occurrence time of an associated activity data of the subject, as the reference activity, and otherwise, set an activity, which has a highest classification value in the triple data, or an activity, which is carried out for a predetermined time, as the reference activity.

According to another aspect of the invention, there is provided a system for recognizing daily activities, the system includes: an activity classification module generating activity classification values by classifying activity data of a subject, received from a sensor attached to a body of the subject; an activity refining module receiving and storing the activity classification values and object response data of objects associated with the activity data of the subject and measured by at least one sensor mounted on the objects, extracting a sudden significant activity data and an unsuitable pattern, which is not suitable for a continuous activity pattern, from the activity classification values, and refining the activity classification values using an activation time of the at least one sensor, mounted on the objects associated with the activity data of the subject; and a daily activity recognition module recognizing daily activities of the subject using the refined activity classification values.

The activity classification module may classify the daily activities of the subject into motions including one of 'sit,' 'walk,' 'run,' 'stand,' 'lie' and 'fall;' postures indicating progressive motions including of 'sitting,' 'standing' and 'lying;' and 'unknown' activities.

The activity classification module may include an input buffer receiving and storing the activity classification values and the object response data; a first refining module extracting a predetermined section of the activity classification values, stored in the input buffer, extracting a sudden significant activity data, which occurs in a time shorter than a minimum time necessary for carrying out an activity corresponding to an activity classification value in the predetermined section, and refining the extracted sudden significant activity data to be identical with an activity classification values preceding and following the sudden significant activity data; and a second refining module, if the sudden significant activity data is absent in the predetermined section, extracting an unsuitable pattern, which is not suitable for a continuous activity pattern of the activity classification values in the predetermined section and refining the unsuitable pattern to be identical with the continuous activity pattern by considering an activation time of the sensor mounted on the objects associated with the activity data of the subject.

According to a further aspect of the invention, there is provided a method for refining subject activity classification, the method includes procedures of: receiving and storing activity classification values of activity data of a subject, measured by a sensor attached to a body of the subject, and object response data measured by at least one sensor mounted on objects; extracting a predetermined section of the stored activity classification values of the subject, judging whether or not a sudden significant activity data is present in the predetermined section, and if the sudden significant activity data is present, refining the sudden significant activity data; and if the sudden significant activity data is absent, judging whether or not activity classification data in the predetermined section are suitable for a continuous activity pattern, if an unsuitable pattern is present, refining the unsuitable pattern by considering an activation time of at least one sensor mounted on an object associated with an activity of the subject.

The procedure of refining the sudden significant activity data may include organizing triple data using continuous three activity classification data in the predetermined section; comparing a short time activity data, which occurs for a time shorter than a minimum time necessary for carrying out an activity included in the triple data, with a preceding activity classification value just prior thereto, and if the short time activity data is not identical with the preceding activity classification value just prior thereto, judging the short time activity data as a sudden significant activity data; and if preceding and following activity classification values are identical, refining the sudden significant activity data using the preceding and following activity classification values.

The procedure of refining of the sudden significant activity data may include, if the short time activity data is identical with the preceding activity classification value just prior thereto, or the preceding and following activity classification values are not identical, judging suitability for a continuous activity pattern.

The procedure of refining the unsuitable pattern may include, if the sudden significant activity data is absent, searching the triple data for an unsuitable pattern, which is not suitable for a continuous activity pattern; setting a reference activity for the triple data; and if an activation time of at least one sensor, mounted on an object associated with the set reference activity, is identical with an occurrence time of the unsuitable pattern, refining the unsuitable pattern using the reference activity.

The procedure of refining the unsuitable pattern may further include, if an activation time of at least one sensor is not identical with an occurrence time of a next continuous activity, refining the unsuitable pattern by matching the triple data with a suitable continuous activity pattern.

The procedure of setting a reference activity may include setting an activity, in which an object response data is simultaneously activated during an occurrence time of an associated activity data of the subject, as the reference activity, and if an activity classification value is not delivered, setting an activity, which has a highest classification value in the triple data, or an activity, which is carried out for a predetermined time, as the reference activity.

The suitable continuous pattern may include at least one selected from the group consisting of 'lie'-'lying,' 'lying'-['sit' or 'stand'], 'sit'-'sitting,' 'sitting'-['stand' or 'lie'], 'stand'-'standing,' 'standing'-['sit' or 'lie' or 'walk' or 'run' or 'fall'], 'fall'-['sit' or 'stand'], 'walk'-['stand' or 'run'] and 'run'-['walk' or 'stand' or 'fall'].

According to the invention as set forth above, in classified subject activities, a sudden significant activity and an unsuitable activity, which is not suitable for a continuous activity pattern, are refined using daily activities of a subject, activation time information of sensors mounted on objects associated with the daily activities of the subject, and the suitability of a continuous activity pattern in relation to the daily activities. This can improve the correctness of subject activity classification that becomes basic information in daily activity analysis.

Accordingly, the invention provides a basis that can improve the correctness of the recognition of daily activities, so that improvement in a home health care service, which provides a service based on the activity information of a subject, can be expected.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE EXEMPLARY EMBODIMENTS

Figure 1:
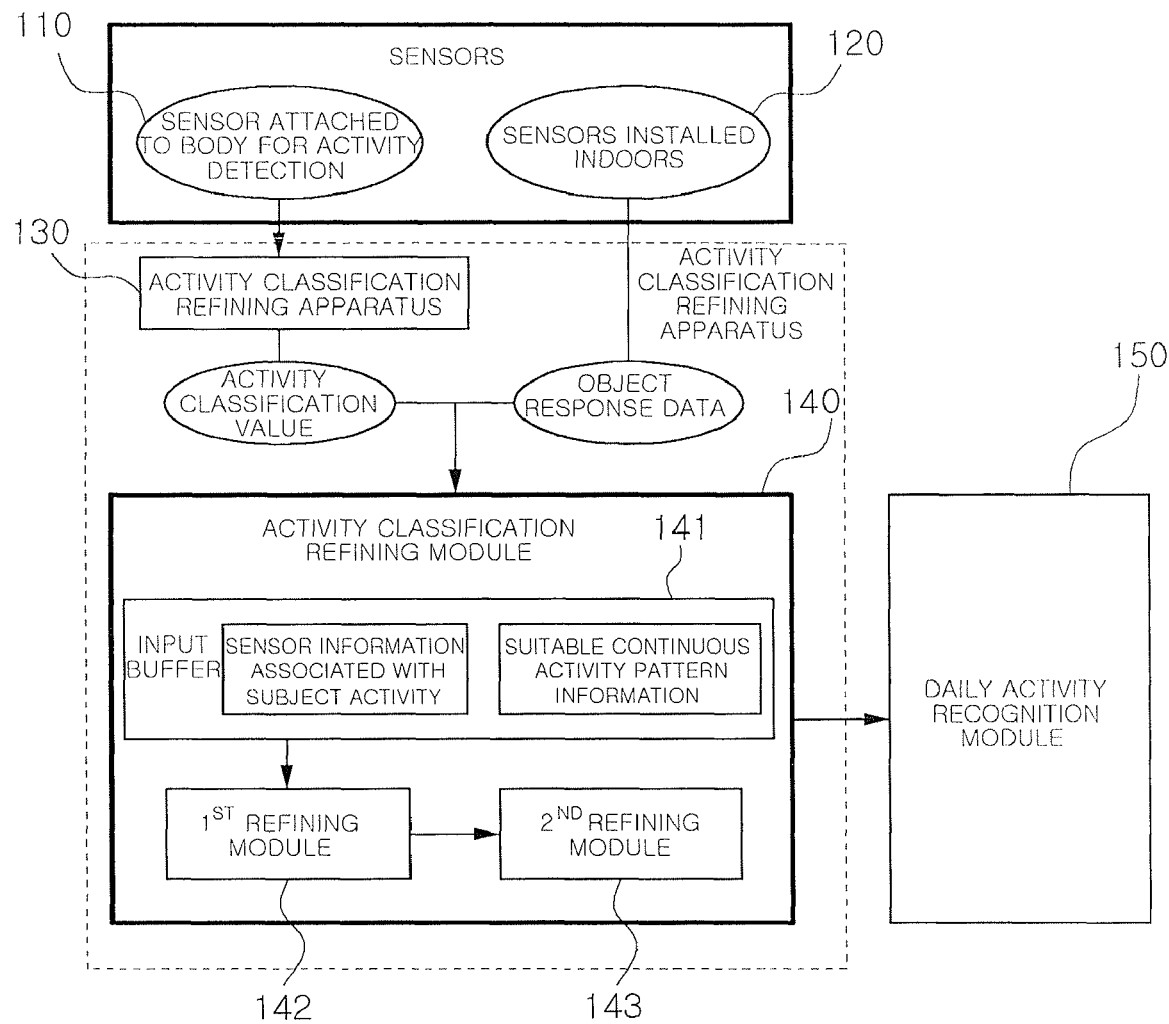
FIG. 1 is a block diagram illustrating the construction of a apparatus for refining activity classification using the refinement of subject activity classification according to an embodiment of the invention, and the overall architecture of a system for recognizing activities using the refining apparatus.

Hereinafter, the present invention will be described more fully in conjunction with the accompanying drawings, in which exemplary embodiments thereof are shown, so that so that this disclosure will be thorough and complete, and will fully convey the scope of the invention to those skilled in the art.

In the following description, well-known functions or constructions by a man skilled in the art are not described in detail since they would obscure the invention in unnecessary detail.

In the drawings, the same reference numerals or letters will be used to designate like or equivalent elements having the same function.

Throughout this specification and the claims that follow, it will be understood that when an element is referred to as being "connected to" or "coupled to" another element, it not only can be "directly connected or coupled to" the other element, but also can be "indirectly connected or coupled to" the other element via an intervening element.

Unless explicitly described to the contrary, the word "comprise (include)," and variations such as "comprises (includes)" or "comprising (including)," will be understood to imply the inclusion of stated elements but not the exclusion of any other elements.

Furthermore, the term "module" means one unit that processes a specific function or action, and can be embodied by one piece of hardware or software or a combination of hardware and software.

FIG. 1 is a block diagram illustrating the construction of an apparatus for refining activity classification for recognition of daily activities according to an embodiment of the invention, and the overall architecture of a system for recognizing activities using the refining apparatus.

In this embodiment of the invention, some sensors such as three axis accelerometers are attached to the body a subject to measure the movement thereof, and other sensors such as pressure sensors are mounted on indoor objects such as a piece of furniture and a floor in order to measure the response of the objects, associated with the movement of the subject.

Various sensors associated with daily activities of the subject can be mounted on the indoor objects. For example, the sensors can be mounted on a bed (for the detection of sleep), a sofa (for the detection of rest), a table and a table chair (for the detection of having a meal), a floor in front of a toile bowl and a lever of the toilet bowl (for the detection of relieving oneself), and a front door floor (for the detection of going out).

These sensors may be implemented as various types of sensors that can measure the movement of the subject and the response of the objects.

As shown in FIG. 1, the apparatus for refining subject activity classification for the recognition of daily activities includes an activity classification module 130 and an activity classification refining module 140.

The activity classification module 130 receives activity data from activity sensors, which are attached to the body of the subject to measure the activity thereof, and classifies the received activity data according to duration times, thereby generating activity classification values.

The activity classification values include the activity data, measured by the activity sensors 110, and the duration times of the activity data.

The activities classified include motions, such as 'sit,' 'walk,' 'run,' 'stand,' 'lie' and 'fall' postures indicating progressive motions, such as 'sitting,' 'standing' and 'lying;' and 'unknown' activities.

The activity classification refining module 140 receives, as input data, the activity classification values from the activity classification module 130, and object response data from sensors 120, which are attached to indoor objects such as a piece of furniture and a floor (hereinafter referred to as "object response sensor").

The activity classification refining module 140 includes an input buffer 141, a first refining module 142 and a second refining module 143, and performs to refine erroneously-sensed activity classification values using the activation time information of the object response sensor 120 and a suitable continuous activity pattern. Here, the activation time information corresponds to the generation time information of response data associated with the subject activities.

The input buffer 141 receives subject activity classification values from the activity classification module 130 to store the received subject activity classification values according to their time sequence, and receives and stores, in real-time, response data from the object response sensors 120 mounted on the objects. The input unit time and the storage time of the activity classification values can be adjusted by a user.

In order to refine a sudden significant activity data, the first refining module 142 organizes triple data by receiving three continuous activity classification values from the input buffer 141.

Then, the first refining module 142 compares a subject activity classification value of the triple data with a preset time. The preset time is a reference time for the classification of subject activities.

As the result of the comparison, if the activity classification value is shorter than a preset time, the corresponding activity is judged as a short time activity (i.e., an activity occurring for a short time). If the short time activity is not identical with a preceding activity just prior thereto, it is judged as a sudden significant activity data, and then refined.

That is, the activity classification values, which precede and follow the sudden significant activity data, are analyzed. If the preceding and following activities are identical, the sudden significant activity data is refined to be identical with the preceding and following activities.

If the short time activity is identical with the preceding activity just prior thereto, it is judged that there is no sudden significant activity data.

If the first refining module 142 judges that there is no sudden significant activity data, the second refining module 143 judges whether or not the activity classification values of the triple data, which are in time sequence, are suitable for a continuous activity pattern. If an unsuitable pattern is present, the second refining module 143 refines the unsuitable pattern.

The subject activity classification values, inputted from the activity classification module 130, and the object response data, inputted from the object response sensor 120 mounted on the objects, include time information regarding the occurrence of subject activities and activation time information.

First, the second refining module 143 sets a reference activity for the refining of an unsuitable pattern, and extracts the activation time of the object response sensor 120, associated with the reference activity, from the input buffer 141.

An activity, in which the object response sensor 120 associated with the subject activity is activated, is preferentially set as the reference activity. If there is not activity, in which the object response sensor 120 is activated, an activity having the highest classification value or an activity carried out for a long time can be set as the reference activity.

Accordingly, the second refining module 143 first checks the activation time of the object response sensor 120, which corresponds to the time when the unsuitable pattern occurs in the triple data. Then, the second refining module 143 refines the unsuitable pattern using the reference activity associated with the object response sensor 120, which is kept activated until the occurrence of the unsuitable pattern, and outputs the refined continuous activity pattern.

If there is no activated object response sensor 120, the second refining module 143 refines the unsuitable pattern to be identical with the suitable continuous activity pattern by matching the suitable continuous activity pattern with the triple data, and outputs the refined continuous activity pattern.

The system for recognizing daily activities through activity classification refinement includes the apparatus for refining subject activity classification according to an embodiment the invention and a daily activity recognition module 150, in which the apparatus for refining subject activity classification includes the sensors 110 and 120, the activity classification module 130 and the activity classification refining module 140.

The daily activity recognition module 150 recognizes daily activities of a subject, such as sleep, rest, meal and going-out, by using a continuous activity pattern having an activity classification value, which is refined by the activity classification refining module 140.

Daily activities of a subject can be recognized as follows: When a sensor attached to a bed is activated, and a refined continuous activity pattern [lying|lying|lying] is maintained for a predetermined time or more, an activity "sleep" is recognized. When a sensor attached to a sofa is activated, and a refined continuous activity pattern [sitting|sitting|sitting] is maintained for a predetermined time or more, an activity "rest" is recognized. When sensors attached to a table and a table chair are activated, and a refined continuous activity pattern [sitting|sitting|sitting] is maintained for a predetermined time or more, an activity "having a meal" is recognized.

Below, a description will be made of a refining method for subject activity classification for the recognition of daily activities according to the invention having the above-described construction.

Figure 2:
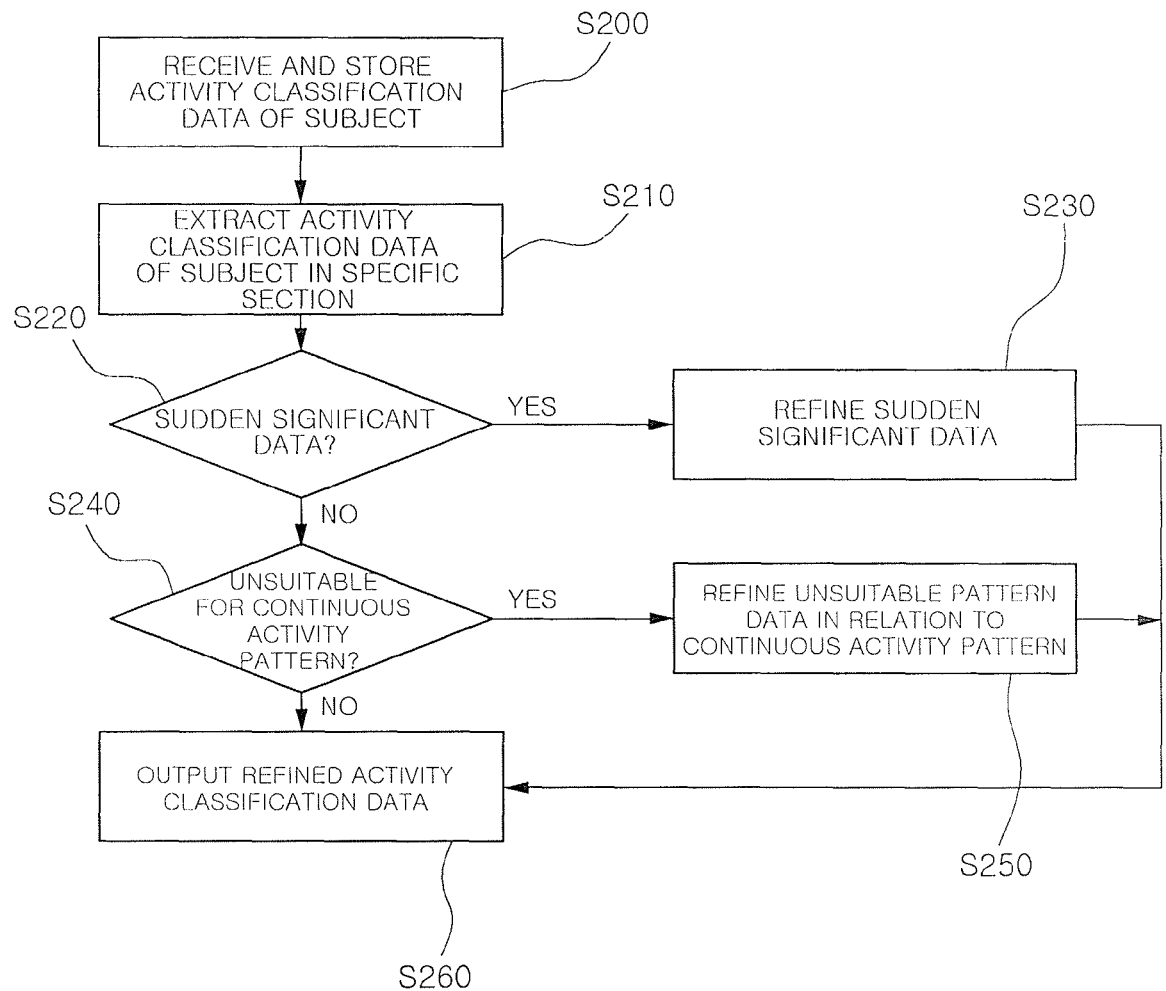
FIG. 2 is a flowchart illustrating a method for refining activity classification for the recognition of daily activities according to the invention.

FIG. 2 is a flowchart illustrating a refining method for activity classification for the recognition of daily activities according to the invention.

First, the input buffer 141 receives and stores subject activity classification values, which are classified (S200).

The first refining module 142 extracts and reads a specific section of the subject activity classification values, stored in the input buffer 141 (S210).

Then, the first refining module 142 judges whether or not a sudden significant activity data is present in subject activity classification values in the specific section (S220), and if the sudden significant activity data is present, refines the sudden significant activity data (S230).

If the sudden significant activity data is absent, the first refining module 142 judges whether or not the subject activity classification values in the specific section are suitable for a continuous activity pattern (S240).

If there is an unsuitable pattern as the result of the judgment in the step S240, the first refining module 142 refines a subject activity classification value, corresponding to the unsuitable pattern, by considering the activation time of the object response sensor 120 associated with the subject activity data (S250).

Alternatively, the first refining module 142 refines the subject activity classification value, corresponding to the unsuitable pattern, by considering suitable continuous activity patterns (S250). Then, a refined activity classification value is outputted (S260).

Figure 3:
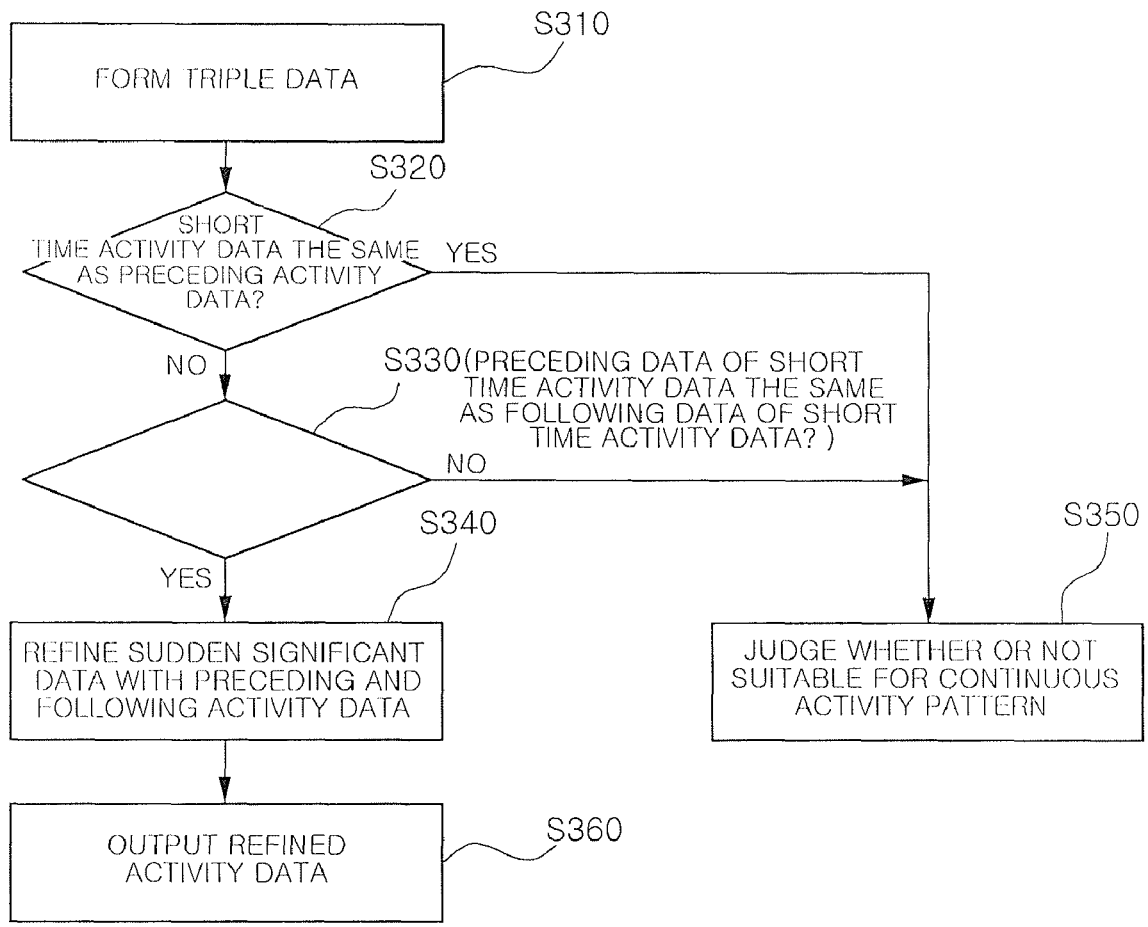
FIG. 3 is a flowchart illustrating a process for refining a sudden significant activity data according to an embodiment of the invention.

FIG. 3 is a flowchart illustrating a process for refining a sudden significant activity data according to an embodiment of the invention.

In S310, the first refining module 142 organizes triple data from continuous three activity classification values, inputted from the input buffer 141.

The first refining module 142 judges a specific activity as a subject activity, only if the specific activity is identically carried out for a predetermined time or more. Accordingly, continuous same activities, occurring for a short time, can also be extracted as a sudden significant subject activity.

In order to prevent this, it is checked whether or not a short time activity (i.e., an activity occurring for a short time) is present in the activity classification values, and if the short time activity is present, the short time activity is compared with a preceding activity just prior thereto. If the short time activity is not identical with the preceding activity just prior thereto, the short time activity is judged as a sudden significant activity (S320).

If the short time activity is identical with the preceding activity just prior thereto, the first refining module 142 judges whether or not suitability for a continuous activity pattern since there is no sudden significant activity data (S350).

After S320, it is judged whether or not preceding and following activity data of the sudden significant activity data are identical (S330), and if the preceding and following activity data are identical, the sudden significant activity data is refined to be identical with the preceding and following activity data (S340).

If the preceding and following activity data are not identical as the result of S330, it is judged whether or not the triple data are suitable for a continuous activity pattern (S350).

If the triple data organized of the continuous three activity classification values, inputted from the input buffer 141 of the activity classification refining module 140, include an unsuitable pattern as the result of S350, an activity data to be refined is extracted and refined. This process will be described in detail with reference to FIG. 4.

For example, a description will be made of an action of the subject in daily life. When the subject lies to sleep or stands, a stop motion such as 'lying' or a motion such as 'lie' is followed by a connecting action such as 'lying' or 'stand,' but not directly by an active motion such as 'run.'

That is, an activity, in which an action such as 'lying,' 'sitting,' 'lie' or 'sit' is followed directly by a specific action such as 'walk' or 'run,' is defined unsuitable for a continuous activity pattern.

The definition of the pattern unsuitable for the continuous activity pattern is assigned to a specific format file, and is set to be correctable by the system.

Figure 4:
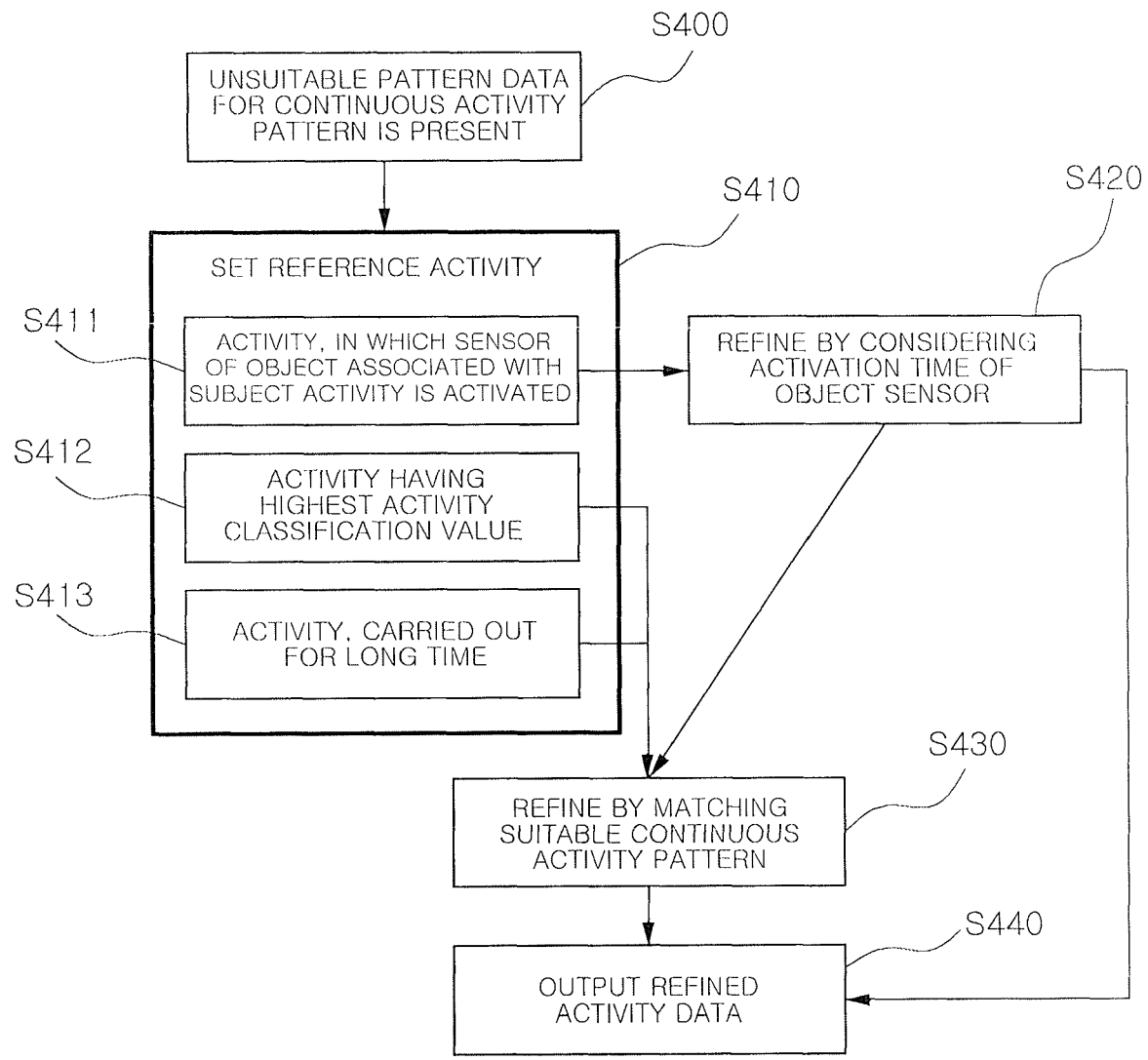
FIG. 4 is a flow diagram illustrating a process of refining an unsuitable pattern, which is not suitable for a continuous activity pattern, using a process time of an object response sensor, associated with a subject activity, according to an embodiment of the present invention.

FIG. 4 is a flow diagram illustrating a process of refining an unsuitable pattern, which is not suitable for a continuous activity pattern, using a process time of the object response sensor 120, associated with a subject activity, according to an embodiment of the present invention.

As the result of the judgment on the triple data whether or not suitable for a continuous activity pattern (S350), if there is an unsuitable pattern (S400), a reference activity for matching the suitable continuous activity pattern with the continuous three activity classification values of the triple data is set (S410).

The reference activity has a preference for an activity, in which the object response sensor 120 is simultaneously activated during the occurrence time of the associated subject activity (S411).

For example, a daily activity, in which the subject takes a sleep, can be deduced from an activity, in which the subject is lying on the bed. That is, it can be appreciated that a subject activity 'lying' is related with the object response sensor 120, which detects an object response when the subject is lying on the bed. Accordingly, the subject activity can be recognized by the sensor.

Typical daily activities of the subject, such as having a meal, relieving oneself, sleep, rest and going-out are associated with specific objects, which are necessary for the recognition of the activities. For example, an activity 'sitting' is associated with objects such as 'table chair,' 'sofa,' 'bed' and 'toilet bowl;' an activity 'lying' is associated with objects such as 'bed' and 'toilet bowl;' and activities such as 'walk,' 'run' and 'standing' are associated with an object 'front door.'

The information of the object response sensor 120, mounted on any of the objects associated with subject activities, is assigned to a specific format file, and is set to be correctable by the system.

If the reference activity, in which the object response sensor 120 associated with the activity of the subject is simultaneously activated, is absent, an activity having the highest classification value in the triple data is set as a reference activity (S412).

If the activity classification values for respective activity classification data, classified by the activity classification module 130, are not delivered, an activity, which was carried out for the longest time, is set as a reference activity (S413).

In the case where the reference activity is set as in the step S411, if an object response sensor 120 associated with the reference activity is kept activated during a time period covering the reference activity and the next following activity, the next following activity is refined to be the reference activity (S420).

For example, when triple data 'sitting'-'walk'-'stand' are inputted, a combination of activities 'sitting'-'walk' is an unsuitable pattern.

If the sensor of an associated object 'table chair' is activated during an activity 'sitting,' the activity is set as the reference activity in the step S411 since the 'table chair' is associated with the activity 'sitting.'

As in the step S420, if the sensor of the 'table chair' is kept activated until the following activity 'walk' connected to the reference activity 'sitting' is carried out, the activity 'walk' is refined to be the reference activity 'sitting.'

Figure 5:
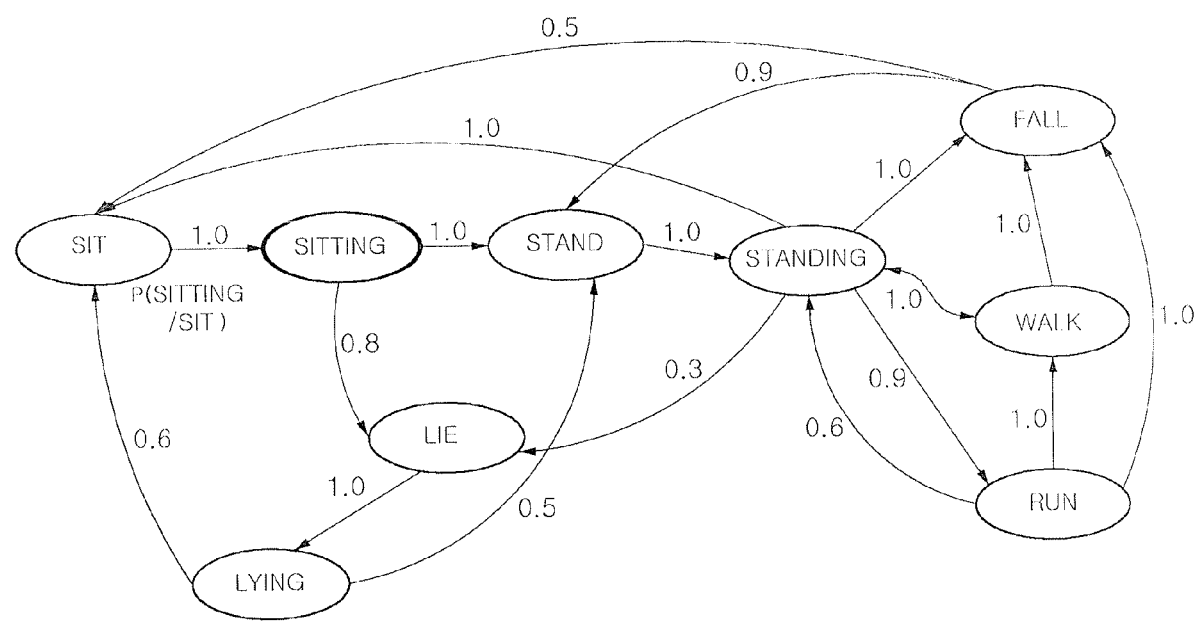
FIG. 5 is a diagram illustrating examples of suitable continuous activity patterns according to the invention.

If not refined as above, the unsuitable pattern is refined by matching a suitable continuous activity pattern as shown in FIG. 5 with triple data (S430).

Then, activity classification data, refined by S420 or S430, are outputted (S440).

FIG. 5 is a diagram illustrating examples of suitable continuous activity patterns of the invention.

The suitable continuous activity patterns are represented by a graph, in which activities are expressed by nodes, and changes in activities are expressed by lines. The changes in activities are also provided with a probability.

The definition of the unsuitable continuous activity pattern is assigned to a specific format file, and is set to be correctable by the system.

Referring to FIG. 5, for example, a change from 'SIT' to 'SITTING' has a probability 1.0, which is expressed by P('SITTING'|'SIT').

The suitable continuous activity patterns basically include 'LIE'-'LYING,' 'LYING'-['SIT'|'STAND'], 'SIT'-'SITTING,' 'SITTING'-['STAND' 'LIE'], 'STAND'-'STANDING,' 'STANDING'-['SIT'|'LIE'|'WALK'|'RUN'|'FALL'], 'FALL'-['SIT' 'STAND'], 'WALK'-['STAND'|'RUN'] and 'RUN'-['WALK'|'STAND'|'FALL'].

As an example of the refinement S430 for the step S412 or S413 of FIG. 4, when the reference activity of <'RUN,' 'SIT,' 'SITTING'> is 'SIT,' an activity to be refined is 'RUN' since 'SITTING' has a path connected to 'SIT'.

Paths including the reference activity are 'STANDING,' 'SIT' and 'SITTING;' 'FALL,' 'SIT' and 'SITTING;' and 'LYING,' 'SIT' and 'SITTING.' The combination probabilities of changing states in respective paths are 1.0, 0.5 and 0.6, sequentially, according to Equations 1 to 3 below:

$$P(\text{STANDING, SIT, SITTING}) = P(\text{SIT}|\text{STANDING}) \cdot P(\text{SITTING}|\text{SIT}) = 1.0 \cdot 1.0 = 1.0 \quad \text{Equation 1}$$

$$P(\text{FALL, SIT, SITTING})=P(\text{SIT}|\text{FALL}) \cdot P(\text{SITTING}|\text{SIT})=0.5 \cdot 1.0=0.5 \quad \text{Equation 2}$$

$$P(\text{LYING, SIT, SITTING})=P(\text{SIT}|\text{LYING}) \cdot P(\text{SITTING}|\text{SIT})=0.6 \cdot 1.0=0.6 \quad \text{Equation 3}$$

Accordingly, a corresponding continuous activity 'RUN' is refined into 'STANDING' according to the path of 'STANDING,' 'SIT' and 'SITTING,' which has the maximum combination probability.

The method of refining activity classification for the recognition of daily activities according to the invention can be written in a computer program.

Those codes and code segments of the computer program are stored in a computer readable medium of the art, and are read and run by a computer to realize a bio-complex investigation method in a protein interaction network using a rule based template.

Examples of the information storage medium include a magnetic recording medium, an optical recording medium and a carrier wave medium.

While the present invention has been described with reference to the particular illustrative embodiments and the accompanying drawings, it is not to be limited thereto but will be defined by the appended claims. It is to be appreciated that those skilled in the art can substitute, change or modify the embodiments in various forms without departing from the scope and spirit of the present invention.

What is claimed is:

1. An apparatus for refining subject activity classification, comprising:
   a computer system comprising a processor and a memory;
   an input buffer on the computer system and configured to receive and store activity classification values of activity data of a subject, wherein the activity data is measured by a sensor attached to a body of the subject and the activity classification values represent activities of the subject, and to receive and store object response data of objects associated with the activity data of the subject, wherein the object response data is measured by at least one object response sensor mounted on the objects and includes an activation time of the sensor;
   a first refining module on the computer system and configured to extract a predetermined number of sequential activity classification values having a pattern and stored in the input buffer; to compare a duration of an activity classification value of the extracted predetermined number of sequential activity classification values to a preset reference time considered necessary for carrying out the activity represented by the activity classification value; to judge the activity represented by the activity classification value as a short time activity when the duration of the activity classification value is shorter than the preset time; to judge the short time activity to be sudden significant activity data when the short time activity is not identical with a preceding activity; and to refine the sudden significant activity data to be identical with activity classification values preceding and following the sudden significant activity data when the preceding and following activities are identical; and
   a second refining module on the computer system and configured to, in response to the first refining module judging there is no sudden significant activity in the predetermined number of sequential activity classification values, judge whether the pattern of the extracted predetermined number of sequential activity classification values is suitable or unsuitable for a continuous activity pattern by comparing the pattern of the extracted sequential activity classification values to stored predetermined suitable or unsuitable continuous activity patterns; check whether the activation time of the at least one object response sensor corresponds to a time when an unsuitable pattern occurs in the extracted predetermined number of sequential activity classification values; and refine the unsuitable pattern to a predetermined suitable pattern corresponding to a reference activity associated with the object response sensor when the object response sensor is activated during the time when the unsuitable pattern occurs.

2. The apparatus of claim 1, wherein the object response data includes occurrence time information of an object response and the activity classification values include occurrence time information of an activity.

3. The apparatus of claim 2, wherein the predetermined section of the activity classification values extracted by the first refining module is triple data, the triple data being three continuous and time sequential activity classification values.

4. The apparatus of claim 3, wherein the second refining module is configured to refine the unsuitable pattern by matching a suitable continuous activity pattern with the triple data when at least one sensor mounted on an object associated with the reference activity is not activated until an occurrence of a following activity classification value.

5. The apparatus of claim 3, wherein the second refining module is configured to set the reference activity to be an activity having a highest classification value in the triple data or an activity carried out for a predetermined time.

6. A system for recognizing daily activities, comprising:
   a computer system comprising a processor and a memory
   an activity classification module on the computer system and configured to generate activity classification values by classifying activity data of a subject, wherein the activity data is received from a sensor attached to a body of the subject and the activity classification values represent activities of the subject;
   an activity refining module on the computer system and configured to receive and store the activity classification values and to receive and store object response data of objects associated with the activity data of the subject, wherein the object response data is measured by at least one object response sensor mounted on the objects, the activity refining module comprising:
   a first refining module configured to extract a predetermined number of sequential activity classification values having a pattern and stored in the input buffer; to compare a duration of an activity classification value of the extracted predetermined number of sequential activity classification values to a preset reference time considered necessary for carrying out the activity represented by the activity classification value; to judge the activity represented by the activity classification value as a short time activity when the duration of the activity classification value is shorter than the preset time; to judge the short time activity to be sudden significant activity data when the short time activity is not identical with a preceding activity; and to refine the sudden significant activity data to be identical with activity classification values preceding and following the sudden significant activity data when the preceding and following activities are identical; and
   a second refining module configured to, in response to the first refining module judging there is no sudden significant activity in the predetermined number of sequential activity classification values, judge whether the pattern of the extracted predetermined number of sequential activity classification values is suitable or unsuitable for a continuous activity pattern by comparing the pattern of the extracted sequential activity classification values to stored predetermined suitable or unsuitable continuous activity patterns; check whether the activation time of the at least one object response sensor corresponds to a time when an unsuitable pattern occurs in the extracted predetermined number of sequential activity classification values; and refine the unsuitable pattern to a predetermined suitable pattern corresponding to a reference activity associated with the object response sensor when the object response sensor is activated during the time when the unsuitable pattern occurs; and a daily activity recognition module on the computer system and configured to recognize daily activities of the subject using the refined activity classification values.

7. The system of claim 6, wherein the activity classification module is configured to classify the daily activities of the subject into motions including any one of 'sit,' 'walk,' 'run,' 'stand,' 'lie' and 'fall', and postures indicating progressive motions, the postures including any one of 'sitting,' 'standing', 'lying;' and 'unknown' activities.

8. The system of claim 7, wherein the activity classification refining module includes:
an input buffer configured to receive and store the activity classification values and the object response data.

9. The system of claim 8, wherein the predetermined section of the activity classification values extracted by the first refining module is triple data, the triple data being three continuous and time sequential activity classification values.

10. The system of claim 9, wherein the second refining module is configured to set the reference activity to be an activity having a highest classification value in the triple data or an activity carried out for a predetermined time.

11. A system for recognizing daily activities, comprising:
a first sensor for attaching to a body of a subject and configured to measure movement of the subject to output activity data of the subject;
at least one object response sensor for installing on objects which the subject interacts with, the at least one object response sensor configured for measuring response of the objects to output object response data;
an activity classification module configured to classify the activity data obtained by the first sensor into activity classification values each representing an activity of the subject;
an activity refining module configured to refine erroneously-sensed activity classification values using activation time information of the object response sensor and a suitable continuous activity pattern, the activity refining module comprising:
an input buffer configured to receive the activity classification values from the activity classification module and to store the received activity classification values in a time sequence, and to receive and store the object response data;
a first refining module configured to extract a predetermined number of sequential activity classification values having a pattern and stored in the input buffer; to compare a duration of an activity classification value of the extracted predetermined number of sequential activity classification values to a preset reference time considered necessary for carrying out the activity represented by the activity classification value; to judge the activity represented by the activity classification value as a short time activity when the duration of the activity classification value is shorter than the preset time; to judge the short time activity to be sudden significant activity data when the short time activity is not identical with a preceding activity; and to refine the sudden significant activity data to be identical with activity classification values preceding and following the sudden significant activity data when the preceding and following activities are identical; and
a second refining module configured to, in response to the first refining module judging there is no sudden significant activity in the predetermined number of sequential activity classification values, judge whether the pattern of the extracted predetermined number of sequential activity classification values is suitable or unsuitable for a continuous activity pattern by comparing the pattern of the extracted sequential activity classification values to stored predetermined suitable or unsuitable continuous activity patterns; check whether the activation time of the at least one object response sensor corresponds to a time when an unsuitable pattern occurs in the extracted predetermined number of sequential activity classification values; and refine the unsuitable pattern to a predetermined suitable pattern corresponding to a reference activity associated with the object response sensor when the object response sensor is activated during the time when the unsuitable pattern occurs.

* * * * *